(12) United States Patent
Zhang et al.

(10) Patent No.: US 10,983,086 B2
(45) Date of Patent: Apr. 20, 2021

(54) REAGENTS FOR POTENTIOMETRIC MAGNESIUM ION SELECTIVE ELECTRODE SENSORS AND METHODS OF PRODUCTION AND USE THEREOF

(71) Applicant: Siemens Healthcare Diagnostics Inc., Tarrytown, NY (US)

(72) Inventors: Wei Zhang, Needham, MA (US); Kevin Horan, Raynham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 442 days.

(21) Appl. No.: 16/059,095

(22) Filed: Aug. 9, 2018

(65) Prior Publication Data

US 2018/0348162 A1 Dec. 6, 2018

Related U.S. Application Data

(63) Continuation of application No. 15/317,688, filed as application No. PCT/US2015/034668 on Jun. 8, 2015.

(60) Provisional application No. 62/011,069, filed on Jun. 12, 2014.

(51) Int. Cl.
*G01N 27/416* (2006.01)
*G01N 33/96* (2006.01)
*G01N 27/333* (2006.01)
*G01N 33/49* (2006.01)

(52) U.S. Cl.
CPC ....... *G01N 27/4163* (2013.01); *G01N 27/333* (2013.01); *G01N 33/96* (2013.01); *G01N 33/49* (2013.01); *G01N 2496/00* (2013.01)

(58) Field of Classification Search
CPC .. G01N 27/4163; G01N 27/333; G01N 33/96; G01N 33/49; G01N 2496/00
See application file for complete search history.

(56) References Cited

U.S. PATENT DOCUMENTS

| 5,667,983 A | 9/1997 | Abel et al. |
| 8,496,800 B2 | 7/2013 | Zhang et al. |
| 2009/0020423 A1 | 1/2009 | Hsiung et al. |
| 2011/0139638 A1* | 6/2011 | Zhang ............... G01N 27/333 205/792 |
| 2017/0030856 A1 | 2/2017 | Zhang et al. |

FOREIGN PATENT DOCUMENTS

| GB | 2080543 A | 2/1982 |
| JP | H08338827 A | 12/1996 |
| JP | 2006300587 A | 11/2006 |
| WO | 8700286 A1 | 1/1987 |
| WO | 9217780 A1 | 10/1992 |
| WO | 9962398 A2 | 12/1999 |

(Continued)

OTHER PUBLICATIONS

International Search Report and Written Opinion of International Application No. PCT/US2015/034668 dated Aug. 21, 2015.

(Continued)

*Primary Examiner* — Maris R Kessel
(74) *Attorney, Agent, or Firm* — Andrew Chien (57) ABSTRACT

Reagents are disclosed for use with potentiometric magnesium ion selective electrodes, along with kits containing same as well as methods of use thereof.

20 Claims, 3 Drawing Sheets

(56) References Cited

FOREIGN PATENT DOCUMENTS

| WO | 2010021923 A1 | 2/2010 |
|---|---|---|
| WO | 2010076717 A1 | 7/2010 |
| WO | 2015160755 A1 | 10/2015 |

OTHER PUBLICATIONS

Wu et al., "Determination of Magnesium and Calcium in Biological Samples by Potentiometric Stripping Analysis", 2010, J. Chin. Chem. Soc. 57(4A): pp. 647-652.

Maj-Zurawska et al., "Fully automated potentiometric determination of ionized magnesium in blood serum", Sep. 1990, Analytica Chimica Acta 236(2), pp. 331-335.

Marsoner et al., "Measurement of ionized magnesium with neutral carrier based ISE's. Progress and results with the AVL 988-4 magnesium analyzer", 1994, Scandinavian Journal of Clinical and Laboratory Investigation, vol. 54, 1994—Issue sup217, pp. 45-51.

Zhang et al., A Comparison of Neutral Mg2+-Selective Ionophores in Solvent Polymeric Membranes: Complex Stoichiometry and Lipophilicity, Jan. 2000, Analytical Sciences, vol. 16 No. 1, pp. 11-18.

Mikhelson et al., "Potentiometric Performance and Interfacial Kinetics of Neutral Ionophore Based ISE Membranes in Interfering Ion Solutions Before and After Contact with Primary Ions", 2001, Electroanalysis 13(10), pp. 876-881.

Lim et al., "Protein adsorption to planar electrochemical sensors and sensor materials", 2004, Pure Appl. Chem., vol. 16, No. 4, pp. 753-764.

Spichiger, "History of the development of magnesium—selective ionophores and magnesium—selective electrodes", 1993, Electroanalysis, vol. 5, pp. 739-745.

Eugster et al., "Characterization procedure for ion-selective electrode assays of magnesium activity in aqueous solutions of physiological composition", May 1993, Clin Chem.; 39(5): pp. 855-859.

O'Donnell et al., "Development of magnesium-selective ionophores", 1993, Analytica Chimica Acta. 281(1): pp. 129-134.

Espadas-Torre et al.,"Thrombogenic Properties of Untreated and Poly(ethylene oxide)-Modified Polymeric Matrices Useful for Preparing Intraarterial Ion-Selective Electrodes", Sep. 15, 1995, Anal. Chem., vol. 67, No. 18, pp. 3108-3114.

Malinowska et al., "Influence of nonionic surfactants on the potentiometric response of ion-selective polymeric membrane electrodes designed for blood electrolyte measurements", Apr. 15, 1998, Anal Chem.;70(8): pp. 1477-1488.

Malinowska et al., "Potentiometric Response of Magnesium-selective Membrane Electrode in the Presence of Nonionic Surfactants", 1999, Analytica Chimica Acta 382(3): pp. 265-275.

Zhang, "Point of Care Testing of Ionized Magnesium in Blood with Potentiometric Sensors—Opportunities and Challenges", 2011, American Journal of Biomedical Sciences, 3(4): pp. 301-312.

Scharbert et al., "Effect of pH levels on platelet aggregation and coagulation: a whole blood in vitro study", 2011, Critical Care vol. 15, Suppl 1: P446; p. S157.

Rayana et al., "Guidelines for sampling, measuring and reporting ionized magnesium in undiluted serum, plasma or blood", 2005, Clin Chem Lab Med.; 43(5): pp. 564-569.

Karlsen, "The Effect of Non-Ionic Surfactants on the Potentiometric Response of Ion Selective Electrodes", Jun. 9, 2009, pp. 1-141.

Vladkova, "Surface Engineering of Blood Contacting Polymeric Biomaterials", 2013, Surface Engineering of Polymeric Biomaterials—Chapter 4, pp. 231-294.

Spichiger et al., "Critical parameters and optimization of a magnesium-selective liquid membrane electrode for application to human blood serum", Jan. 1, 1991, Fresenius' Journal of Analytical Chemistry, vol. 341; No. 12; pp. 727-731.

Zhang et al., "An impedance study of Mg<2+>-selective membranes", Mar. 1, 2000, Electrochimica Acta, Elsevier Science Publishers, Barking, GB, vol. 45, No. 14, pp. 2259-2266.

European Search Report and Written Opinion of European Application No. 15806492.3 dated May 29, 2017.

* cited by examiner

REAGENTS FOR POTENTIOMETRIC MAGNESIUM ION SELECTIVE ELECTRODE SENSORS AND METHODS OF PRODUCTION AND USE THEREOF

CROSS REFERENCE TO RELATED APPLICATIONS/INCORPORATION BY REFERENCE STATEMENT

The subject application is a continuation of U.S. Ser. No. 15/317,688, filed Dec. 9, 2016; which is a US national stage application filed under 35 USC § 371 of International Application No. PCT/US2015/034668, filed Jun. 8, 2015; which claims benefit under 35 USC § 119(e) of U.S. provisional Application No. 62/011,069, filed Jun. 12, 2014. The entire contents of each of the above-referenced patent applications are hereby expressly incorporated herein by reference.

BACKGROUND

The use of ion selective electrodes (ISEs) to determine the presence and quantity of various analytes in biological samples has become a useful diagnostic technique. Indeed, ISEs have been used to detect analytes such as magnesium, sodium, potassium, calcium, and chloride, among others. Some of these ISEs are often housed within clinical diagnostic instruments for simultaneous analysis of a large number of analytes.

One such use of the ISEs is for the determination of the amount of magnesium ions in a biological sample, specifically blood. Blood comprises many ions; the main ions present are magnesium ions ($Mg^{2+}$), calcium ions ($Ca^{2+}$), and sodium ions ($Na^+$). For each type of ion, ISEs have a different response kinetic pattern, which causes the data to be greatly skewed if the ISEs are not calibrated to take into account the different selectivities of the ions. Currently, the calibration of potentiometric ISEs for measuring ionized magnesium ("Mg ISE") generally encompasses calibrating the Mg ISE with three calibration reagents which characterize the slope, intercept, and selectivity of the magnesium ions against the calcium ions.

DESCRIPTION OF THE SEVERAL VIEWS OF THE DRAWINGS

As illustrated in FIG. 1, the planar Mg ISE had an unstable recovery period for the first 3 to 5 days after coming in contact with each of these quality control reagents.

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and/or claimed herein can be made and executed without undue experimentation in light of the present disclosure. While the compositions and methods of this presently disclosed and/or claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more, or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20%, or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "purified" as used herein means at least one order of magnitude of purification is achieved compared to the starting material or of the natural material, for example but not by way of limitation, two, three, four, or five orders of magnitude of purification of the starting material or of the natural material. Thus, the term "purified" as utilized herein does not necessarily mean that the material is 100% purified, and therefore such term does not exclude the presence of other material(s) present in the purified composition.

The term "sample" as used herein will be understood to include any type of biological sample that may be utilized in accordance with the presently disclosed and/or claimed inventive concept(s). Examples of biological samples that may be utilized include, but are not limited to, whole blood or any portion thereof (i.e., plasma or serum), saliva, sputum, cerebrospinal fluid (CSF), skin, interstitial fluid, tears, mucus, urine, swabs, combinations, and the like.

The term "wetup" as used herein will be understood to refer to the hydration process from the installation of a sensor in an analyzer to a point at which a stable signal is obtained out of calibration reagents.

The term "recovery" as used herein, either alone or in connection with another term (for example but without limitation, "quality control recovery," "recovery period," and "recovery elevation"), is understood to mean the yield of an analytical process with comparison to an assigned value(s) or reference value(s).

Issues with the current methods of calibrating ISEs for measuring magnesium ions stem from the calibration reagents that are currently used. These calibration reagents have been found to cause planar Mg ISE sensors to undergo a rapid wetup during the first few days after calibration, resulting in heightened response kinetics, and sometimes taking a week or more until the sensor is capable of providing reproducible measurements. Such a long wetup time significantly shortens the useable lifespan of the sensor and prevents new and/or recently calibrated sensors from being readily useable.

It has previously been determined that the pattern of rapid wetup and the resulting change in response kinetics for Mg ISEs is associated with the ratio of calcium ions to magnesium ions in the calibration reagents. This is due to the Mg ISEs having different response kinetics for calcium ions and magnesium ions. Specifically, the ionophores in Mg ISEs have previously been found to have an ionophore:$Mg^{2+}$ and ionophore:$Ca^{2+}$ stoichiometry of 1:1 and 2:1, respectively. See W. Zhang et al. (*Analytical Sciences* (2000) 16:11-18), which is hereby incorporated by reference in its entirety. This difference in stoichiometry values suggests that the ionophores for Mg ISEs may have a higher selectivity for calcium ions than magnesium ions and, therefore, the ratio of $Ca^{2+}$ to $Mg^{2+}$ should be calibrated to take into account this selectivity.

It was reported that the ratio of $Ca^{2+}$ to $Mg^{2+}$ in solution affects the response kinetics of Mg selective electrodes (i.e., the time to steady state). In general, the effect is produced by different rates of dehydration of the magnesium and calcium ions, the latter rate apparently being higher [see, for example, Maj-Zurawska et al. (*Analytica Chimica Acta* (1990) 236:331-335); Mikhelson et al. (*Electroanalysis* (2001) 13:876-881); Marsoner et al. (*Scand J Clin Lab Invest* (1994) 54(suppl 217):45-51); and Zhang et al. (*Analytical Sciences*, incorporated supra)]. The kinetic discrimination of calcium and magnesium ions may be associated with the role of these ions in all processes at the membrane/solution interface, including the calcium/magnesium biological pump or ion channel. During the initial wetup period, the $Mg^{2+}$ ISE membrane/solution interface has a very dynamic dehydration process for the $Mg^{2+}$ and $Ca^{2+}$ ions, along with different kinetics for each ion. When the $Ca^{2+}$:$Mg^{2+}$ ratio in solution is relatively low, the net rate of dehydration for $Ca^{2+}$ and $Mg^{2+}$ at the membrane/solution interface may lead to unstable recovery evaluation of aqueous samples (e.g., QC) and calibration response signals (see FIG. 1), which could thus lead to significantly skewed measurements.

As described and/or claimed herein, it was presently discovered that increasing the amount of $Ca^{2+}$ in the calibration reagents to a level wherein the ratio of $Ca^{2+}$:$Mg^{2+}$ is similar to that of whole blood minimizes the impact of the initial wetup period; the presently disclosed and/or claimed inventive concept(s) determined that, when the calibration reagent has the same (or substantially similar) kinetic pattern as the whole blood samples to be tested, the Mg ISE can be effectively calibrated for measuring the magnesium ion content in blood. Additionally, applying the same $Ca^{2+}$:$Mg^{2+}$ ratio to the quality control reagents and wash reagents likewise minimizes deviations in measurements taken using the quality control reagents or after washing the magnesium sensing membranes in the Mg ISEs.

It is to such reagents, as well as compositions, kits, and methods related thereto, that the presently disclosed and/or claimed inventive concept(s) is directed.

Turning now to embodiments of the presently disclosed inventive concept(s), new and improved reagents are provided that can be used with Mg sensors such that the Mg sensors exhibit increased stability and improved response kinetics over prior art sensor/reagent combinations. The reagents of the presently disclosed and/or claimed inventive concept(s) can be used as calibration, quality control, and/or wash reagents, and may be utilized with potentiometric ISEs for ionized magnesium, wherein the sensor/reagent combination exhibits improved response kinetics and recovery stability during the initial period after calibrating the potentiometric ISEs for measuring ionized magnesium. In certain embodiments, the new and improved reagents can be used, in particular, with a solid-state planar magnesium sensing membrane for a potentiometric ion selective electrode that detects ionized magnesium in a biological sample.

In the presently disclosed and/or claimed inventive concept(s), the reagent is provided with a $Ca^{2+}$ to $Mg^{2+}$ distribution ratio that is substantially similar to the ratio found in the biological sample to be tested. In one embodiment, the biological sample is whole blood, which has a normal distribution ratio of $Ca^{2+}$ to $Mg^{2+}$ of around 2:1. Therefore, the reagent of this embodiment comprises calcium ions and magnesium ions in a calcium:magnesium molar ratio in a range of from about 1.5 to about 3.25, such as but not limited to, a range of from about 1.7 to 3.25, or a range of from about 1.9 to about 2.1. In one particular embodiment, the reagent comprises calcium ions and magnesium ions in a calcium:magnesium molar ratio of 2:1.

In certain embodiments, the reagent may have a pH in a range of from about 6 to about 8, or from about 6.5 to about 7.8, or from about 6.8 to about 7.2. In addition, the reagent may include additional components. For example but not by way of limitation, the reagent may further include one or more additional ions. Any other ion known in the art or otherwise contemplated herein may be present in the reagent and at any concentration, so long as the reagent and the potentiometric ion selective electrode can function in accordance with the presently disclosed and/or claimed inventive concept(s). For example but not by way of limitation, the reagent may further include sodium ions. In one particular embodiment, the reagent may further comprise at least 50 mmol/L of sodium ions.

In other embodiments, the reagent may further comprise one or more surfactants. Any surfactant(s) known in the art or otherwise contemplated herein may be present in the reagent and at any concentration, so long as the reagent and the potentiometric ion selective electrode can function in accordance with the presently disclosed and/or claimed inventive concept(s). In certain embodiments, the surfactant present in the reagent may be a poly(ethylene oxide) surfactant, wherein the poly(ethylene oxide) surfactant may be utilized at any concentration that allows the reagent and the potentiometric ion selective electrode to function in accordance with the presently disclosed and/or claimed inventive concept(s). A non-limiting example of a poly(ethylene oxide) surfactant concentration that falls within the scope of the presently disclosed and/or claimed inventive concept(s) is less than about 100 mg/L.

Any poly(ethylene) surfactants known or otherwise contemplated within the art are capable of functioning as described herein and may be utilized in accordance with the presently disclosed and/or claimed inventive concept(s). Non-limiting examples of poly(ethylene oxide) surfactants that may be utilized in accordance with the presently disclosed and/or claimed inventive concept(s) are represented by the structures of formulas I-III, as shown below.

Formula I

Formula II

Formula III

In Formula I, n is in a range of from about 9 to about 10; in Formula III, n is about 100. One non-limiting example of a surfactant represented by the structure of Formula I (for example, t-octylphenoxypolyethoxyethanol) is sold under the trade name TRITON™ X-100 (Sigma-Aldrich, St. Louis, Mo.). One non-limiting example of a surfactant represented by the structure of Formula II (for example, polyoxyethylene 23 lauryl ether) is known in the art by the product designation BRIJ® 35 (CAS No. 9002-92-0). A non-limiting example of a surfactant represented by the structure of Formula III (wherein n is about 100) is polyoxyethylene(100) stearyl ether nonionic surfactant, which is known in the art by the product designation BRIJ® 700 (CAS No. 9005-00-9). Particular non-limiting examples of the surfactants represented by the structure of Formula III are disclosed in U.S. Pat. No. 8,496,900, issued to Zhang et al. on Jul. 30, 2013.

In one embodiment, the reagent is a quality control reagent, wherein the quality control reagent can be either an internal quality control reagent or an external quality control reagent. As used herein, an internal quality control reagent (also referred to as an "automatic quality control reagent") is contained within the potentiometric ion selective electrode apparatus and comes into contact with the magnesium sensing membrane at a pre-determined time and/or after a pre-determined event, wherein the pre-determined time/event may be mechanically or electronically programmed into the potentiometric ion selective electrode. Additionally, as used herein, an external quality control reagent is a quality control reagent that is initially separate (i.e., external) from the potentiometric ion selective electrode apparatus and is made to come into contact with the magnesium sensing membrane at a pre-determined time and/or after a pre-determined event by actions of an operator of the potentiometric ion selective electrode apparatus.

Another embodiment of the presently disclosed and/or claimed inventive concept(s) is directed to a method of calibrating a magnesium sensing membrane for a potentiometric ion selective electrode. In the method, the magnesium sensing membrane is contacted with one or more of the calibration reagents described or otherwise contemplated herein above. In one particular embodiment, the presently disclosed and/or claimed inventive concept(s) is directed to a method of calibrating a solid-state planar magnesium sensing membrane for a potentiometric ion selective electrode, wherein a solid-state planar magnesium sensing membrane is contacted with one or more calibration reagents(s) described or otherwise contemplated herein above. In one particular embodiment, the method of calibrating the magnesium sensing membrane for a potentiometric ion selective electrode comprises contacting the magnesium sensing membrane with at least three separate calibration reagents described or otherwise contemplated herein above to characterize the slope, intercept, and selectivity against calcium ions.

Another embodiment of the presently disclosed and/or claimed inventive concept(s) is directed to a method of monitoring the quality control of a magnesium sensing membrane for a potentiometric ion selective electrode. In the method, the magnesium sensing membrane is contacted with one or more of the reagents described or otherwise contemplated herein above. In one particular embodiment, the presently disclosed and/or claimed inventive concept(s) is directed to a method of monitoring the quality control of a solid-state planar magnesium sensing membrane for a potentiometric ion selective electrode. In the method, a solid-state planar magnesium sensing membrane is contacted with one or more of the reagents described or otherwise contemplated herein above, wherein at least one reagent is a quality control reagent. In the method of monitoring the quality control of a magnesium sensing membrane for a potentiometric ion selective electrode, the magnesium sensing membrane may be contacted with at least three separate quality control reagents described or otherwise contemplated herein above to characterize the slope, intercept, and selectivity against calcium ions.

Another embodiment of the presently disclosed and/or claimed inventive concept(s) is directed to a method of washing a magnesium sensing membrane for a potentiometric ion selective electrode. In the method, the magnesium sensing membrane is contacted with one or more of the wash reagents described or otherwise contemplated herein above. In particular, the presently disclosed and/or claimed inventive concept(s) is directed to a method of washing a solid-state planar magnesium sensing membrane for a potentiometric ion selective electrode; in the method, a solid-state planar magnesium sensing membrane is contacted with one or more of the wash reagents described or otherwise contemplated herein above.

While certain embodiments of the reagents described and contemplated herein may be disclosed as being a "calibration reagent," a "quality control reagent," or a "wash reagent," it is to be understood that these designations are not to be perceived as limiting; a single formulation of reagent may possess two or three of the calibration, quality control, and/or wash functions. Therefore, while the above methods are disclosed as requiring a "calibration reagent," a "quality control reagent," or a "wash reagent," this requirement is simply based upon the function of the reagent and not on the composition thereof. A single reagent may be capable as functioning as two or more of a calibration reagent, a quality control reagent, and a wash reagent. Thus, it will be understood that the methods of (i) calibrating, (ii) monitoring the quality control of, and (iii) washing a magnesium sensing membrane may all utilize a single reagent composition that is capable of providing all three functions.

Yet other embodiments of the presently disclosed and/or claimed inventive concept(s) are directed to kits that include one or more of any of the reagents described or otherwise contemplated herein. When two or more reagents are present, the combination of reagents may be of the same function and/or different function. In one embodiment, the kit may include at least one calibration reagent, at least one quality control reagent, at least one wash reagent, or any combination thereof. For example but not by way of limitation, the kit may include at least one calibration reagent, at least one quality control reagent, and at least one wash reagent. In other embodiments, the kit may include combinations of reagents that possess the same function. For example but not by way of limitation, the kit may include at least three calibration reagents; in addition, this kit may further include at least three quality control reagents and/or at least one wash reagent.

The kits of the presently disclosed and/or claimed inventive concept(s), which include one or more of any of the reagents or combinations of reagents described or otherwise contemplated herein, may further include a solid-state planar magnesium PVC (polyvinyl chloride) sensing membrane for a potentiometric magnesium ion selective electrode. Any solid-state planar magnesium PVC sensing membrane known in the art or otherwise contemplated herein may be utilized in accordance with the presently disclosed and/or claimed inventive concept(s). Non-limiting examples of membranes that may be utilized include, but are not limited to, membrane formulations containing $Mg^{2+}$ ionophores of malondiamide derivatives, as well as those disclosed in Zhang et al. (*Analytical Sciences*, incorporated supra) and Lim et al. (*Pure Appl. Chem.* (2004) 75:753-764). Non-limiting examples of specific ionophores that may be utilized include, but are not limited to, Tris(malondiamides) derivatives (such as but not limited to, ETH5506, ETH5504, ETH7025, ETH3832, K22B5, and the like), as well as those disclosed in Zhang et al. (*Analytical Sciences*, incorporated supra). Other non-limiting examples of specific membranes, ionophores, and lipophilic salts that may be utilized include those disclosed in Maj-Zurawska et al., Mikhelson et al., and Marsoner et al. (all incorporated supra). The entire contents of each of the above references are hereby expressly incorporated herein.

Another non-limiting example of a magnesium sensing membrane for a potentiometric ion selective electrode that may be utilized in accordance with the presently disclosed and/or claimed inventive concept(s) is disclosed in co-pending Application U.S. Ser. No. 61/981,277, filed Apr. 18, 2014, which is hereby expressly incorporated herein in its entirety.

In certain embodiments, the kits of the presently disclosed and/or claimed inventive concept(s), which include one or more of any of the reagents or combinations of reagents described or otherwise contemplated herein, may further include a potentiometric magnesium ion selective electrode comprising the solid-state planar magnesium membrane as described herein above.

In addition, the kits may further contain other reagent(s) for conducting any of the particular methods described or otherwise contemplated herein. The nature of these additional reagent(s) will depend upon the particular assay format, and identification thereof is well within the skill of one of ordinary skill in the art.

The components/reagents may each be disposed in separate containers/compartments of the kit, or various components/reagents can be combined in one or more containers/compartments of the kit, depending on the competitive nature of the components/reagents and/or the stability of the components/reagents. The kit can further include other separately packaged reagents for conducting an assay. The relative amounts of the various components/reagents in the kits can vary widely to provide for concentrations of the components/reagents that substantially optimize the reactions that need to occur during the assay methods and further to optimize substantially the stability/sensitivity of an assay. Positive and/or negative controls may be included with the kit. The kit can further include a set of written instructions explaining how to use the kit. For example, but not by way of limitation, the kit may further include instructions for using the reagents to rinse, calibrate, operate, and/or monitor quality control of the potentiometric ion selective electrode. A kit of this nature can be used in any of the methods described or otherwise contemplated herein.

EXAMPLE

An Example is provided hereinbelow. However, the presently disclosed and/or claimed inventive concept(s) is to be understood to not be limited in its application to the specific experimentation, results, and laboratory procedures disclosed herein below. Rather, the Example is simply provided as one of various embodiments and is meant to be exemplary, not exhaustive.

In this Example, the instability of QC (AQC) recovery of a potentiometric magnesium ion selective electrode was studied over a uselife of four weeks. As shown herein below, reformulation of the calibration reagents utilized with the ISE to provide the reagents to provide the desired $Ca^{2+}$:$Mg^{2+}$ ratio improved the performance stability of the Mg sensor.

Figure 1:
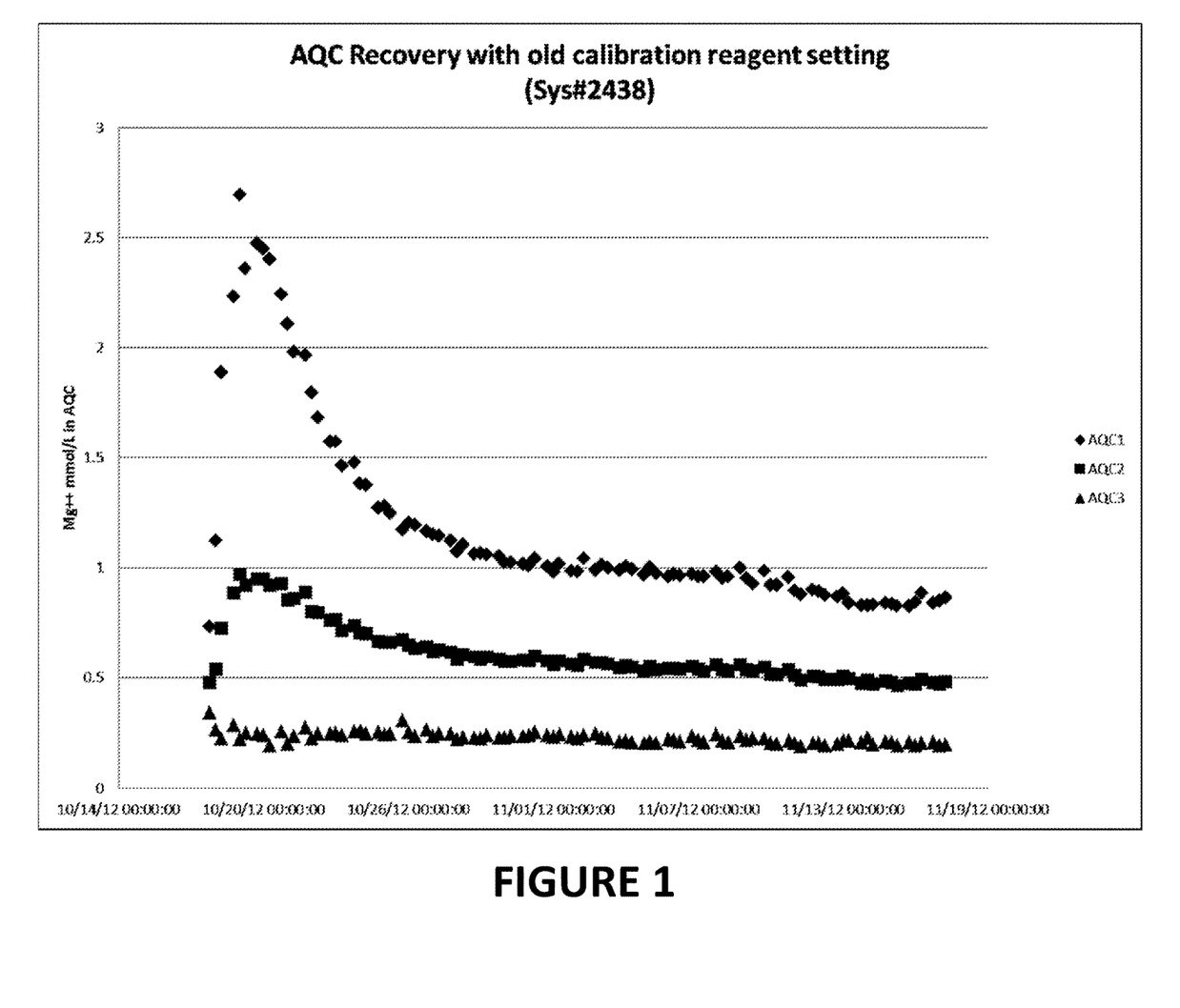
FIG. 1 illustrates the quality control recovery of a planar Mg ISE sensor that was calibrated with the three calibration reagents that have decreased target amounts of $Mg^{2+}$. AQC1 (diamonds), AQC2 (squares), and AQC3 (triangles) have target $Mg^{2+}$ concentrations of 0.9 mmol/L, 0.6 mmol/L, and 0.3 mmol/L, respectively. Each of the three calibrators has a $Ca^{2+}:Mg^{2+}$ ratio of 1.14 to 1.34.

FIG. 1 shows an AQC recovery plot of the response data obtained using a potentiometric ISE with a solid-state planar magnesium sensing membrane that was calibrated with calibration reagents of the prior art. One of three prior art calibration reagents had a $Ca^{2+}$:$Mg^{2+}$ ratio of about 1.34. Three aqueous QC samples were tested at three different target $Mg^{2+}$ concentrations (AQC1: 0.9 mmol/L; AQC2: 0.6 mmol/L; and AQC3: 0.3 mmol/L). The sensor had blood contact since installation.

As can be seen, unstable recovery plots were observed at all three levels of AQCs tested, especially during the first week of uselife. The "humps" observed over the first 5-10 days of uselife indicate that the $Mg^{2+}$ concentrations of the reagents were incorrectly detected at a level as much as 2×-3× above their actual concentration during this time. This observation of "hump" QC recovery is explained by slow dynamic complexation between the magnesium ion ionophore in the sensor membrane and the $Ca^{2+}$ and $Mg^{2+}$ ions in the calibration reagents. The stoichiometry number between ionophore:$Mg^{2+}$ is believed to be 1:1, and the stoichiometry number between ionophore and $Ca^{2+}$ is believed to be 2:1 (see Zhang et al., *Analytical Sciences*, incorporated supra).

Figure 2:
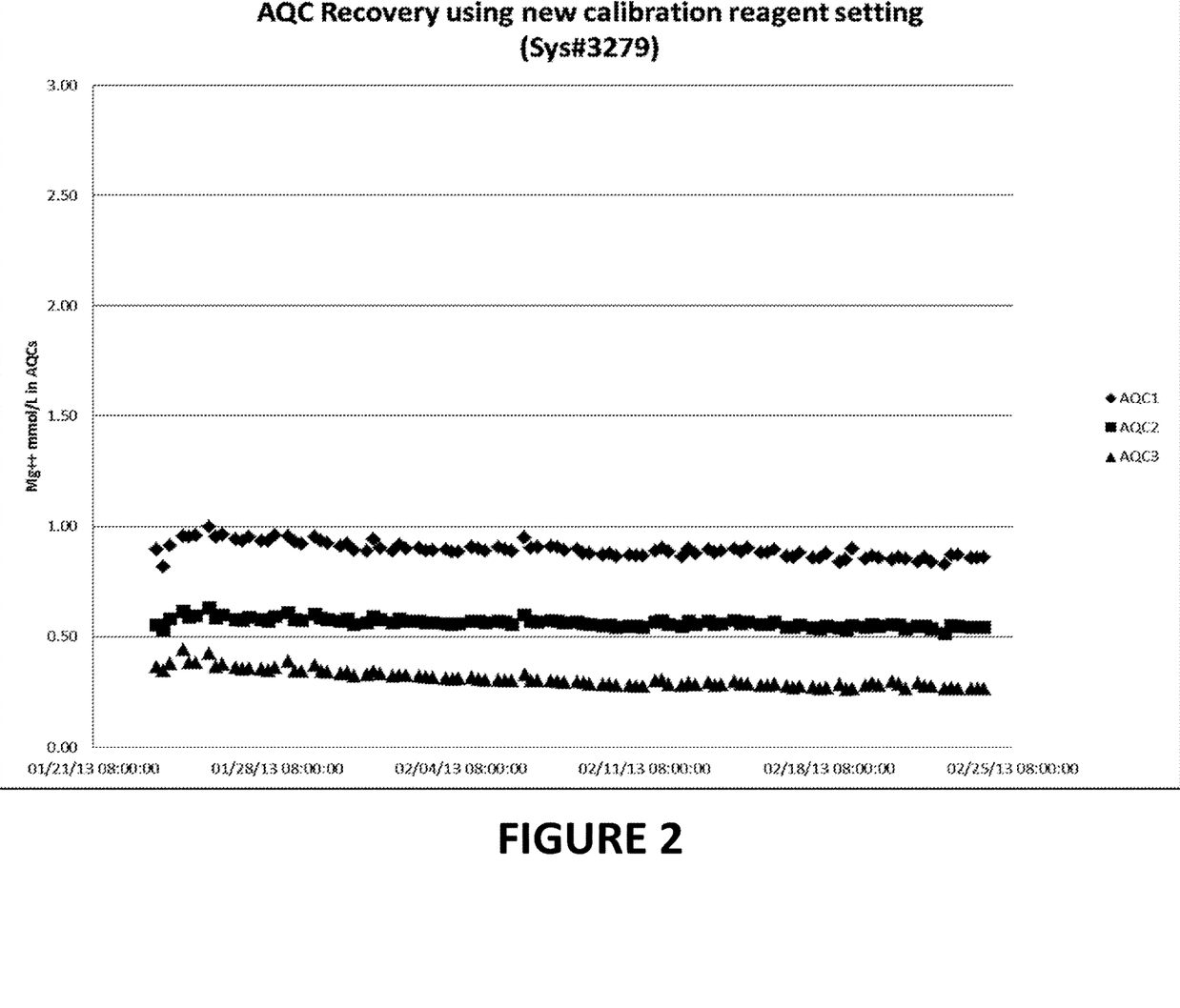
FIG. 2 illustrates the quality control recovery of a planar Mg ISE calibrated with three calibration reagents constructed in accordance with the presently disclosed and/or claimed inventive concept(s). All three calibration reagents have a $Ca^{2+}:Mg^{2+}$ ratio greater than 1.5. Like in FIG. 1, AQC1 (diamonds), AQC2 (squares), and AQC3 (triangles) have target $Mg^{2+}$ concentrations of 0.9 mmol/L, 0.6 mmol/L, and 0.3 mmol/L, respectively. However, in this Example, AQC1 (diamonds), AQC2 (squares), and AQC3 (triangles) have $Ca^{2+}:Mg^{2+}$ ratios of 1.57, 1.92, and 2.89, respectively. As can be seen, the planar Mg ISE has a stable initial recovery period that lasts throughout the lifespan of the magnesium sensing membrane of the ISE.

In contrast, FIG. 2 illustrates an AQC recovery plot of the response data obtained using a potentiometric ISE with a solid-state planar magnesium sensing membrane that was calibrated with calibration reagents of the presently disclosed and/or claimed inventive concept(s) that possessed a $Ca^{2+}$:$Mg^{2+}$ ratio above the prior art level of <1.5. These calibration reagents had $Ca^{2+}$:$Mg^{2+}$ ratios in a range of from about 1.7 to about 3.25 (i.e., 1.57 for AQC1, 1.92 for AQC2, and 2.89 for AQC3), and the reagents were tested at the same three target $Mg^{2+}$ concentrations (AQC1: 0.9 mmol/L; AQC2: 0.6 mmol/L; and AQC3: 0.3 mmol/L). As above, the sensor had blood contact since installation.

Unlike the prior art reagents, the substantially linear lines of FIG. 2 indicate stable recovery plots over the entire uselife window for all three levels of AQCs tested. These stable response data measurements for the useable life of the magnesium sensor were observed when the ratio of $Ca^{2+}$:$Mg^{2+}$ is increased to be above 1.5 and closer to (or above) 2, which is the approximate $Ca^{2+}$:$Mg^{2+}$ ratio for whole blood samples. It is believed that a calibration reagent setting of a $Ca^{2+}$:$Mg^{2+}$ ratio in a range of from about 1.7 to about 3.25 helps build up dynamic equilibria between ionophore in the solid state sensor and the $Ca^{2+}$ and $Mg^{2+}$ ions in the calibration reagents.

It has been determined herein that, if the ratio of $Ca^{2+}$:$Mg^{2+}$ is too far below 2:1 (i.e., 1.5:1 or lower) during the initial contact period between the sensor membrane and the calibration reagents, it leads to a slow procedure to reach complexation equilibrium between the ionophore and the $Mg^{2+}$ and $Ca^{2+}$ ions in the magnesium sensing membrane of the ISE (i.e., at the membrane interface and in the membrane bulk), as seen in FIG. 1 and described herein above. When the sensor contacts a blood sample during the initial period, the adsorbed protein layer functions as an ion-exchanger that responds to electrolytes following the normal distribution ratio in blood for $Ca^{2+}$ and $Mg^{2+}$ ($Ca^{2+}$=1.2 mmol/L to $Mg^{2+}$=0.5 mmol/L). As such, the presently disclosed and/or claimed inventive concept(s) have determined that a ratio of $Ca^{2+}$:$Mg^{2+}$ in reagents should be close to 2:1 so that the sensor has identical performance in all reagents (calibration reagents, Wash, AQCs, etc.).

Figure 3:
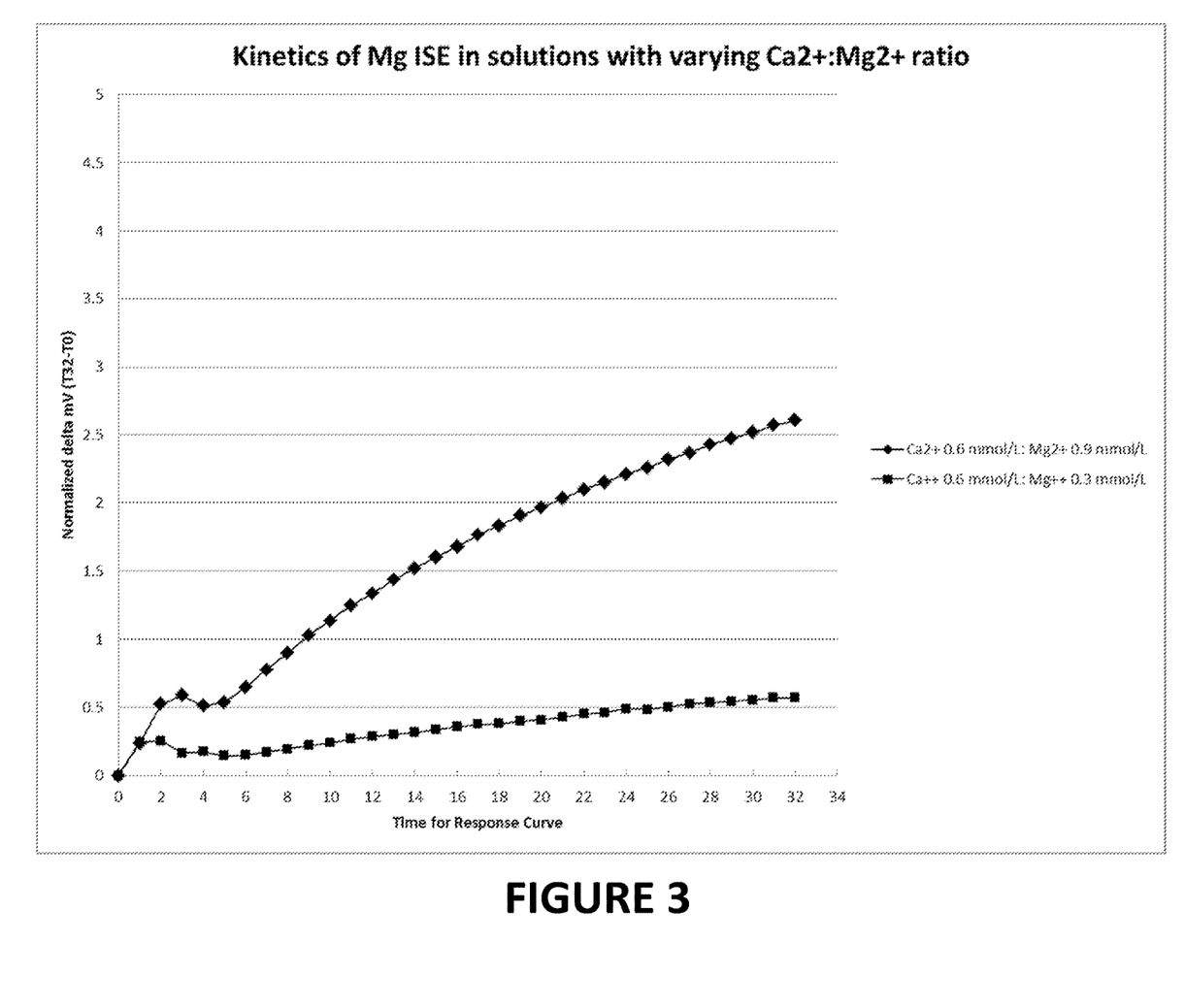
FIG. 3 illustrates the variation in response kinetics for a planar Mg ISE in solutions with varying $Ca^{2+}:Mg^{2+}$ ratios. Normalized Delta mV=mV (t32)−mV (t0), which stands for mV difference between the end point at 32 seconds and initial point at 0 seconds.

In a calibration setting containing two to three calibration reagents, if one reagent has a $Ca^{2+}$:$Mg^{2+}$ ratio that is well below 2:1 (e.g., <1.5), the thermodynamic complexation process between ionophore and $Mg^{2+}$ and $Ca^{2+}$ ions will be sluggish (FIG. 3). It will take a long time to buildup a steady-state membrane potential response in all reagents when they possess different $Ca^{2+}$:$Mg^{2+}$ ratios (membrane potential=phase boundary potential+membrane diffusion potential), ultimately leading to an unstable initial response period. Adjusting the $Ca^{2+}:Mg^{2+}$ ratio in all of the reagents (i.e., all calibration, wash, and QC reagents utilized with a particular ISE) to a ratio in the range of from about 1.5 to about 3.25 will accelerate such thermodynamic process. Thus, the $Mg^{2+}$ sensor can reach a steady-state potential response in all reagents.

Additionally, ionic strength in all of the reagents should be adequately high enough (i.e., an ionic strength between at least 50-160 mmol/L) so that the concentration values of $Mg^{2+}$ and $Ca^{2+}$ are not significantly affected by activity coefficient differences among the reagents. As shown in Table 1, ionic strength (IS) has a significant impact on the molal activity variation of divalent cations. If one of the calibration reagents has an IS of 50 mmol/L ($Na^+$) and the other calibration reagent(s) has an IS of 125 mmol/L, the molal activity variation of the divalent cation cannot be neglected. For $Mg^{2+}$ and $Ca^{2+}$ concentrations of 0.5 mmol/L and 1.2 mmol/L, respectively, the molal activities of the cations are 0.21 mmol/L ($Mg^{2+}$) and 0.44 mmol/L ($Ca^{2+}$) in 125 mmol/L $Na^+$ solution. However, in 25 mmol/L $Na^+$ solution, the molal activities of the cations become 0.29 mmol/L ($Mg^{2+}$) and 0.66 mmol/L ($Ca^{2+}$). Since a potentiometric sensor responds only to the molal activity (as opposed to the mass concentration), molal activity variation induced by ionic strength can lead to biased calibration results (slope, selectivity, and intercept). With such biased calibration parameters, blood sample recovery can be wrongly calculated.

TABLE 1

Impact of Ionic Strength on Activity Coefficient and Molal Activity of Cations in Aqueous Solution

|  | Ionic Strength ($Na^+$, mmol/L) | $K^+$ (4 mmol/L) | $Ca^{2+}$ (1.2 mmol/L) | $Mg^{2+}$ (0.5 mmol/L) |
|---|---|---|---|---|
| Activity coefficient | 150 | 0.713 | 0.348 | 0.398 |
|  | 125 | 0.729 | 0.367 | 0.414 |
|  | 100 | 0.747 | 0.391 | 0.436 |
|  | 75 | 0.770 | 0.424 | 0.464 |
|  | 50 | 0.800 | 0.471 | 0.505 |
|  | 25 | 0.844 | 0.553 | 0.578 |
|  | 10 | 0.889 | 0.652 | 0.667 |
| Molal activity (mmol/L) | 150 | 2.85 | 0.42 | 0.20 |
|  | 125 | 2.92 | 0.44 | 0.21 |
|  | 100 | 2.99 | 0.47 | 0.22 |
|  | 75 | 3.08 | 0.51 | 0.23 |
|  | 50 | 3.20 | 0.57 | 0.25 |
|  | 25 | 3.38 | 0.66 | 0.29 |
|  | 10 | 3.56 | 0.78 | 0.33 |

Therefore, in accordance with the presently disclosed and/or claimed inventive concept(s), there have been provided reagents, as well as kits containing same and methods of use thereof, that fully satisfy the objectives and advantages set forth hereinabove. Although the presently disclosed and/or claimed inventive concept(s) has been described in conjunction with the specific drawings, experimentation, results, and language set forth herein above, it is evident that many alternatives, modifications, and variations will be apparent to those of ordinary skill in the art. Accordingly, it is intended to embrace all such alternatives, modifications, and variations that fall within the spirit and broad scope of the presently disclosed and/or claimed inventive concept(s).

The following is a numbered list of non-limiting, illustrative embodiments of the inventive concepts disclosed herein:

1. A reagent for a solid-state planar magnesium sensing membrane for a potentiometric ion selective electrode that detects ionized magnesium in a biological sample, the reagent comprising calcium ions and magnesium ions present in a calcium:magnesium molar ratio in a range of from about 1.5:1 to about 3.25:1.

2. The reagent of illustrative embodiment 1, wherein the calcium:magnesium molar ratio is in a range of from about 1.7:1 to about 3.25:1.

3. The reagent of illustrative embodiment 1, wherein the calcium:magnesium molar ratio is about 2:1.

4. The reagent of any of illustrative embodiments 1 to 3, wherein the reagent has a pH in a range of from about 6 to about 8.

5. The reagent of any of illustrative embodiments 1 to 3, wherein the reagent has a pH in a range of from about 6.5 to about 7.8.

6. The reagent of any of illustrative embodiments 1 to 5, further comprising sodium ions at a concentration of at least 50 mmol/L.

7. The reagent of any of illustrative embodiments 1 to 6, further comprising a surfactant.

8. The reagent of illustrative embodiment 7, wherein the surfactant comprises a poly(ethylene oxide) surfactant.

9. The reagent of illustrative embodiment 8, wherein the poly(ethylene oxide) surfactant is represented by the structure of formula I:

Formula I wherein n is in the range of from about 9 to about 10.

10. The reagent of illustrative embodiment 8, wherein the poly(ethylene oxide) surfactant is represented by the structure of formula II:

Formula II.

11. The reagent of illustrative embodiment 8, wherein the poly(ethylene oxide) surfactant is represented by the structure of formula III:

Formula III wherein n is 100.

12. The reagent of illustrative embodiment 8, wherein the concentration of the poly(ethylene oxide) surfactant is less than about 100 mg/L.

13. The reagent of any of illustrative embodiments 1 to 12, wherein the reagent is a calibration reagent.

14. The reagent of any of illustrative embodiments 1 to 12, wherein the reagent is a quality control reagent.

15. The kit of illustrative embodiment 14, wherein the quality control reagent is an external quality control reagent.

16. The kit of illustrative embodiment 14, wherein the quality control reagent is an internal quality control reagent.

17. The reagent of any of illustrative embodiments 1 to 12, wherein the reagent is a wash reagent.

18. A method of calibrating a solid-state planar magnesium sensing membrane for a potentiometric ion selective electrode comprising the step of contacting a solid-state planar magnesium sensing membrane with the calibration reagent of illustrative embodiment 13.

19. A method of monitoring the quality control of a solid-state planar magnesium sensing membrane for a potentiometric ion selective electrode comprising the step of contacting a solid-state planar magnesium sensing membrane with the quality control reagent of illustrative embodiment 14.

20. A method of washing a magnesium sensing membrane for a potentiometric ion selective electrode comprising the step of contacting a solid-state planar magnesium sensing membrane with the wash reagent of illustrative embodiment 17.

21. A kit comprising: at least one calibration reagent of illustrative embodiment 13.

22. The kit of illustrative embodiment 21, wherein the at least one calibration reagent is further defined as at least two calibration reagents, and wherein each calibration reagent is a calibration reagent of illustrative embodiment 13.

23. The kit of illustrative embodiment 21, further comprising: at least one quality control reagent of illustrative embodiment 14; and/or at least one wash reagent of illustrative embodiment 17.

24. The kit of illustrative embodiment 19, wherein the at least one calibration reagent is further defined as at least three calibration reagents, and wherein each calibration reagent is a calibration reagent of illustrative embodiment 13, and wherein the kit further comprises: at least three quality control reagents of illustrative embodiment 14; and at least one wash reagent of illustrative embodiment 17.

25. A kit comprising: at least one calibration reagent of illustrative embodiment 13; and a potentiometric ion selective electrode comprising a solid-state planar magnesium sensing membrane.

26. The kit of illustrative embodiment 25, wherein the at least one calibration reagent is further defined as at least two calibration reagents, and wherein each calibration reagent is a calibration reagent of illustrative embodiment 13.

27. The kit of illustrative embodiment 25, further comprising: at least one quality control reagent of illustrative embodiment 14; and/or at least one wash reagent of illustrative embodiment 17.

28. The kit of illustrative embodiment 25, wherein the at least one calibration reagent is further defined as at least three calibration reagents, and wherein each calibration reagent is a calibration reagent of illustrative embodiment 13, and wherein the kit further comprises: at least three quality control reagents of illustrative embodiment 14; and at least one wash reagent of illustrative embodiment 17.

What is claimed is:

1. A method of calibrating a solid-state planar magnesium sensing membrane for a potentiometric ion selective electrode that detects ionized magnesium in a biological sample, the method comprising:
calibrating the magnesium sensing membrane with at least three separate calibration reagents, wherein each of the calibration reagents comprises calcium ions and magnesium ions present in a calcium:magnesium molar ratio in a range of from about 1.5:1 to about 3.25:1, and wherein the at least three separate calibration reagents are provided with the same calcium:magnesium molar ratio.

2. The method of claim 1, wherein the calcium:magnesium molar ratio in each of the reagents is in a range of from about 1.7:1 to about 3.25:1.

3. The method of claim 1, wherein the calcium:magnesium molar ratio in each of the reagents is about 2:1.

4. The method of claim 1, wherein each of the calibration reagents has a pH in a range of from about 6 to about 8.

5. The method of claim 1, wherein at least one of the calibration reagents has a pH in a range of from about 6.5 to about 7.8.

6. The method of claim 1, wherein each of the calibration reagents further comprises sodium ions at a concentration of at least 50 mmol/L.

7. The method of claim 1, wherein each of the calibration reagents further comprises a surfactant, and wherein the same surfactant is present in each of the calibration reagents.

8. The method of claim 7, wherein the surfactant present in each calibration reagent comprises a poly(ethylene oxide) surfactant.

9. The method of claim 8, wherein the poly(ethylene oxide) surfactant is represented by the structure of formula I:

Formula I wherein n is in the range of from about 9 to about 10.

10. The method of claim 8, wherein the poly(ethylene oxide) surfactant is represented by the structure of formula II:

Formula II.

11. The method of claim 8, wherein the poly(ethylene oxide) surfactant is represented by the structure of formula III:

Formula III wherein n is 100.

12. The method of claim 8, wherein the concentration of the poly(ethylene oxide) surfactant present in each calibration reagent is less than about 100 mg/L, and wherein the same concentration of surfactant is present in each of the calibration reagents.

13. The method of claim 1, further comprising the step of contacting the magnesium sensing membrane with at least one additional reagent selected from a wash reagent and a quality control reagent, wherein the at least one additional reagent comprises calcium ions and magnesium ions present at the same calcium:magnesium molar ratio as the at least three calibration reagents.

14. The method of claim 1, wherein the magnesium sensing membrane is subjected to multiple calibrations with the at least three separate calibration reagents and is stable for at least four weeks.

15. A method of calibrating a solid-state planar magnesium sensing membrane for a potentiometric ion selective electrode that detects ionized magnesium in a biological sample, the method comprising:
calibrating the magnesium sensing membrane with at least three separate calibration reagents, wherein each of the calibration reagents comprises calcium ions and magnesium ions present in a calcium:magnesium molar ratio in a range of from about 1.5:1 to about 3.25:1, and wherein the at least three separate calibration reagents are provided with the same calcium:magnesium molar ratio, and wherein all of the reagents comprises a poly(ethylene oxide) surfactant selected from the group consisting of:
(a) the poly(ethylene oxide) surfactant is represented by the structure of formula I:

Formula I wherein n is in the range of from about 9 to about 10;
(b) the poly(ethylene oxide) surfactant is represented by the structure of formula II:

Formula II and
(c) the poly(ethylene oxide) surfactant is represented by the structure of formula III:

Formula III wherein n is 100.

16. The method of claim 15, wherein each one of the reagents has a pH in a range of from about 6 to about 8, and wherein each of the reagents further comprises sodium ions at a concentration of at least 50 mmol/L.

17. The method of claim 15, further comprising the step of contacting the magnesium sensing membrane with at least one additional reagent selected from a wash reagent and a quality control reagent, wherein the at least one additional reagent comprises calcium ions and magnesium ions present at the same calcium:magnesium molar ratio as the at least three calibration reagents.

18. The method of claim 15, wherein the magnesium sensing membrane is subjected to multiple calibrations with the at least three separate calibration reagents and is stable for at least four weeks.

19. A method of calibrating a solid-state planar magnesium sensing membrane for a potentiometric ion selective electrode that detects ionized magnesium in a biological sample, the method comprising:

calibrating the magnesium sensing membrane with at least three separate calibration reagents, wherein each of the calibration reagents comprises:
calcium ions and magnesium ions present in a calcium:magnesium molar ratio in a range of from about 1.5:1 to about 3.25:1, wherein the at least three separate calibration reagents are provided with the same calcium:magnesium molar ratio;
a pH in a range of from about 6 to about 8;
sodium ions at a concentration of at least 50 mmol/L; and
a poly(ethylene oxide) surfactant selected from the group consisting of:
(a) the poly(ethylene oxide) surfactant is represented by the structure of formula I:

Formula I wherein n is in the range of from about 9 to about 10;
(b) the poly(ethylene oxide) surfactant is represented by the structure of formula II:

Formula II; and
(c) the poly(ethylene oxide) surfactant is represented by the structure of formula III:

Formula III wherein n is 100;
contacting the magnesium sensing membrane with at least one additional reagent selected from a wash reagent and a quality control reagent, wherein the at least one additional reagent comprises calcium ions and magnesium ions present at the same calcium:magnesium molar ratio as the at least three calibration reagents; and
wherein the magnesium sensing membrane is subjected to multiple calibrations with the at least three separate calibration reagents and is stable for at least four weeks.

20. The method of claim 19, wherein the concentration of the poly(ethylene oxide) surfactant present in each calibration reagent is less than about 100 mg/L, and wherein the same concentration of surfactant is present in each of the calibration reagents.

* * * * *